United States Patent
Francischelli

[19]

[11] Patent Number: 6,086,526

[45] Date of Patent: Jul. 11, 2000

[54] CARDIAC ASSISTANCE SYSTEM

[75] Inventor: David Francischelli, Anoka, Minn.

[73] Assignee: Medtronic, Inc., Minneapolis, Minn.

[21] Appl. No.: 08/834,015

[22] Filed: Apr. 11, 1997

[51] Int. Cl.[7] ........................................... A61M 1/10

[52] U.S. Cl. ......................................... 600/16; 623/3

[58] Field of Search ................................. 128/898–899; 600/16, 17; 623/3

[56] References Cited

U.S. PATENT DOCUMENTS

| | | | |
|---|---|---|---|
| 4,979,936 | 12/1990 | Stephenson et al. | 600/16 |
| 5,007,927 | 4/1991 | Badylak et al. | 623/3 |
| 5,647,380 | 7/1997 | Campbell et al. | 600/16 X |
| 5,683,455 | 11/1997 | Tilmons | 623/3 |
| 5,758,664 | 6/1998 | Campbell et al. | 600/16 X |
| 5,814,102 | 9/1998 | Guldner et al. | 623/3 |

*Primary Examiner*—Francis J. Jaworski
*Attorney, Agent, or Firm*—Thomas F. Woods; Michael J. Jaro; Harold Patton

[57] ABSTRACT

A system to provide cardiac assistance to a patient's heart. The system includes a pulse generator adapted to be coupled to patient's heart and adapted to be coupled to a skeletal muscle ventricle (SMV). The system further includes a sewing ring adapted to be coupled to the SMV and adapted to be coupled to the patient's circulatory system, the sewing ring has a flexible cylindrical sleeve having a distal end and a proximal end, the flexible cylindrical sleeve defining a lumen therewithin, the ring further features a means for maintaining the patency of the lumen, the means for maintaining the patency positioned on the proximal end. In the preferred embodiment the means for maintaining the patency of the lumen is a reinforcing ring mounted to the proximal end of the flexible cylindrical sleeve, preferably a silicone ring.

21 Claims, 6 Drawing Sheets

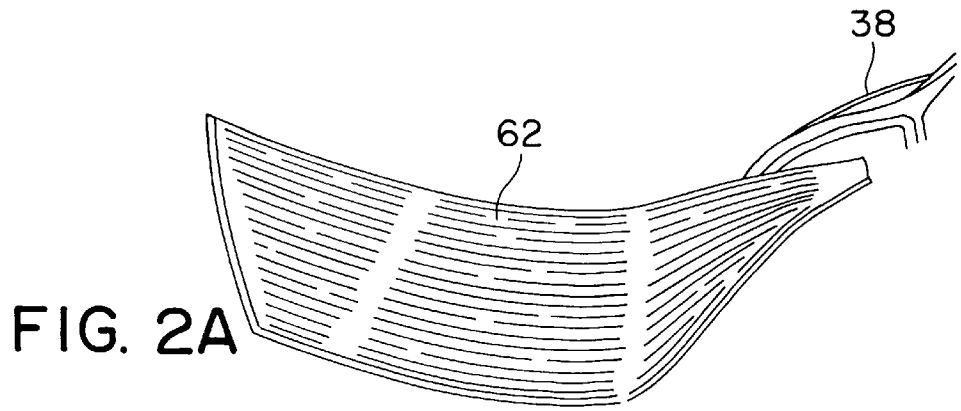
FIG. 2A
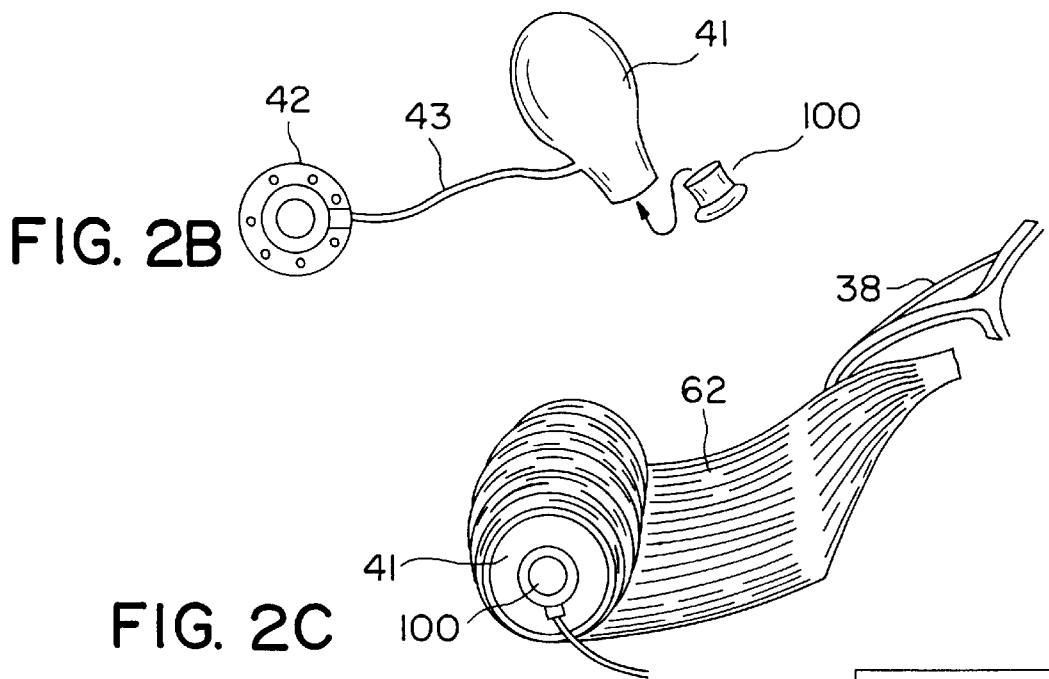
FIG. 2B
FIG. 2C
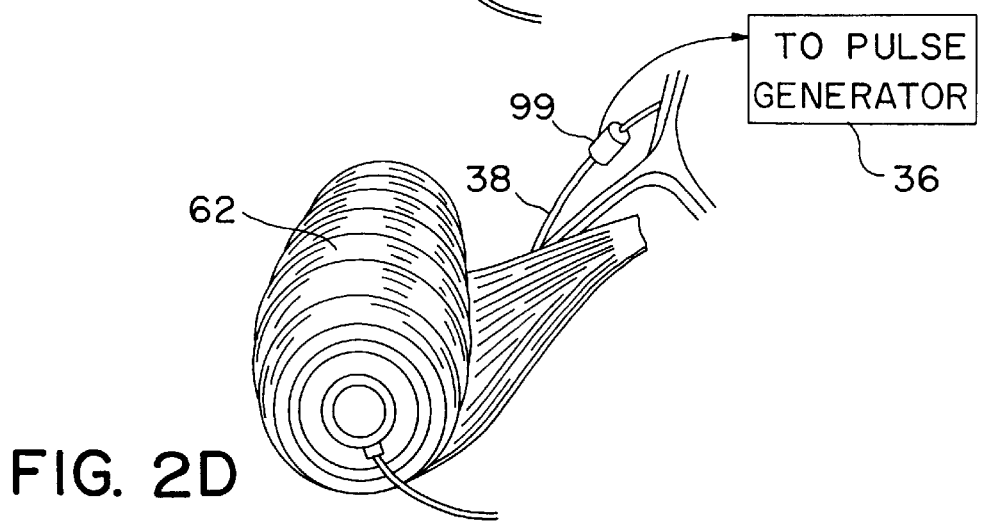
FIG. 2D

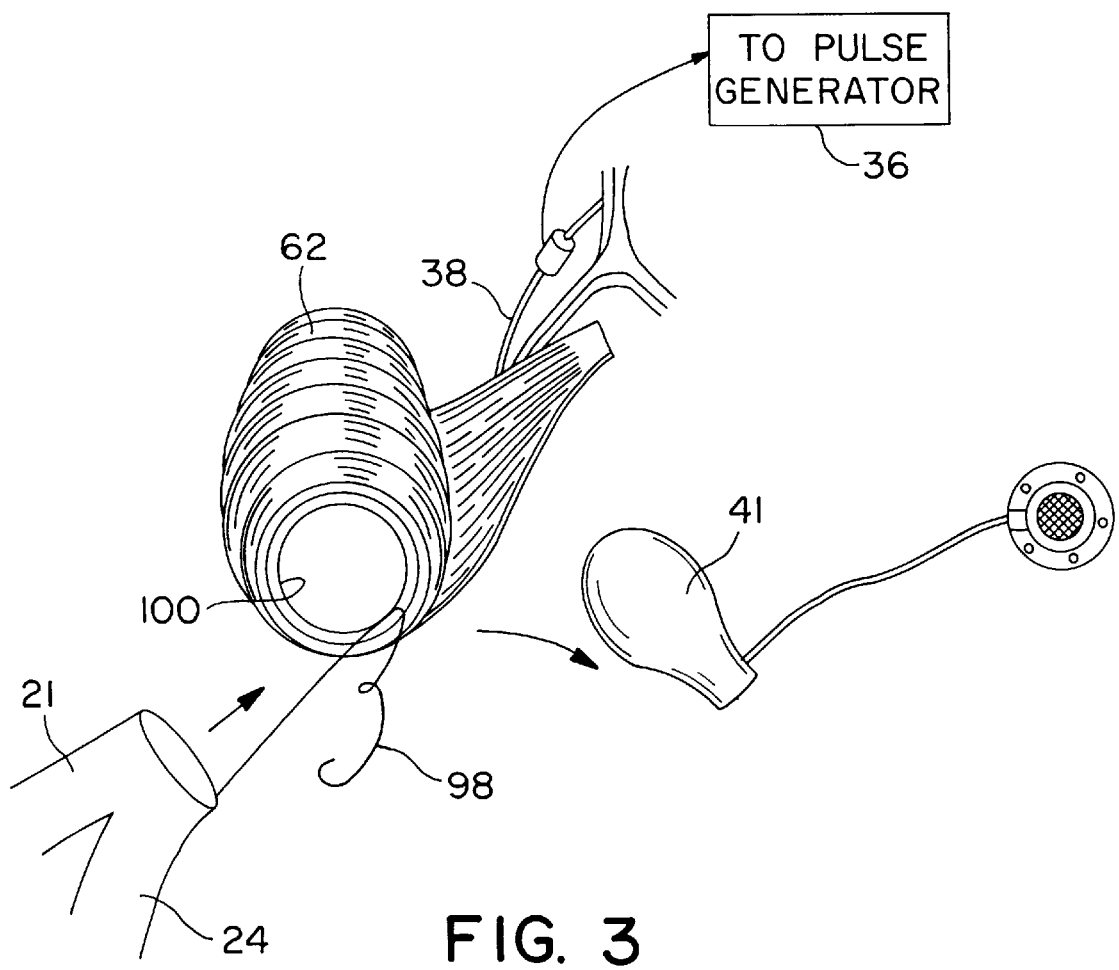
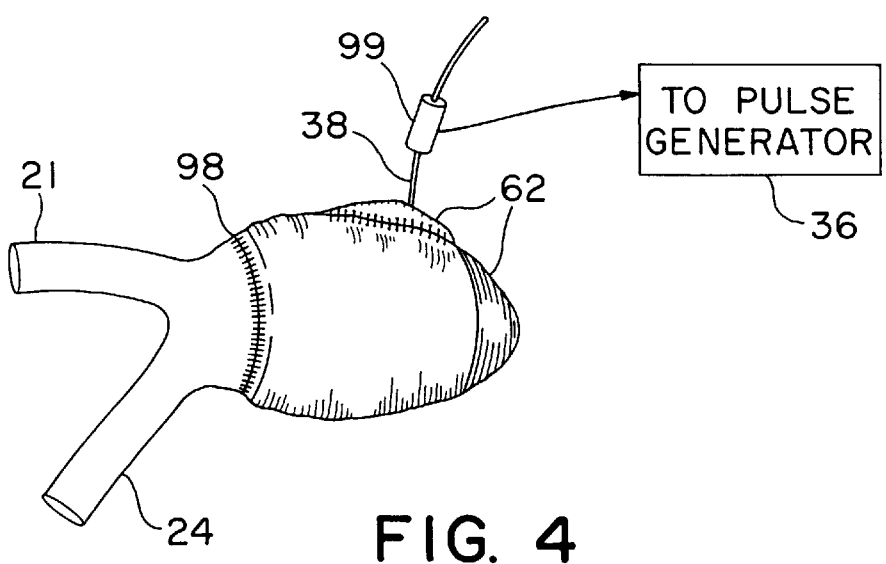

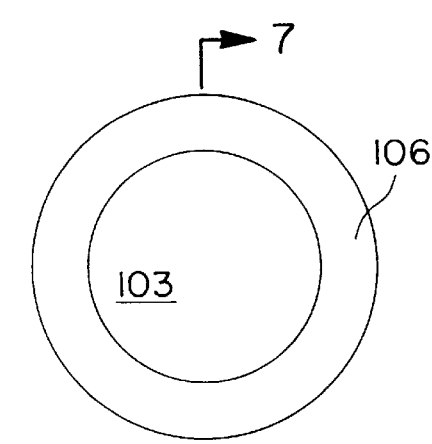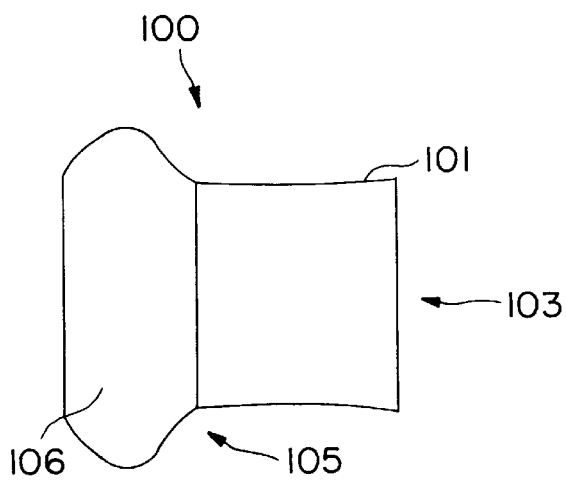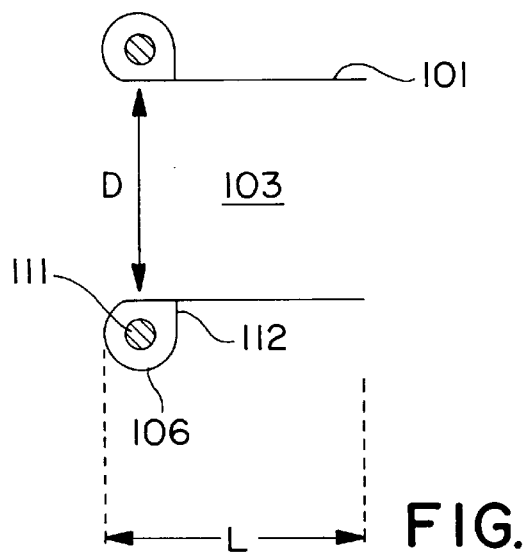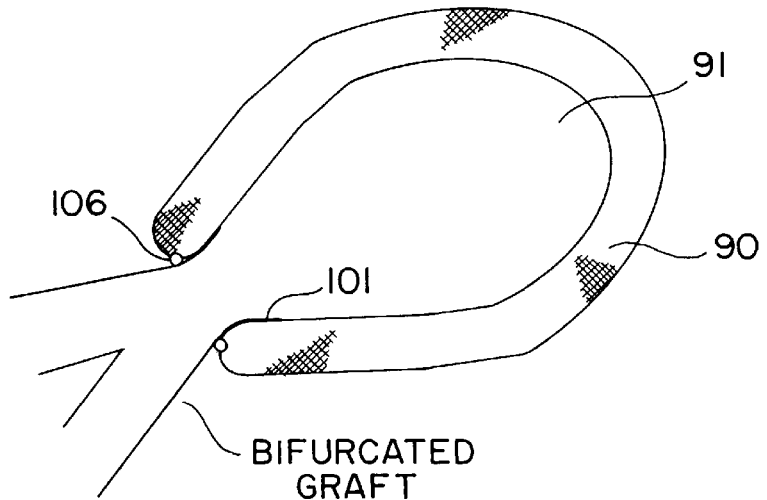

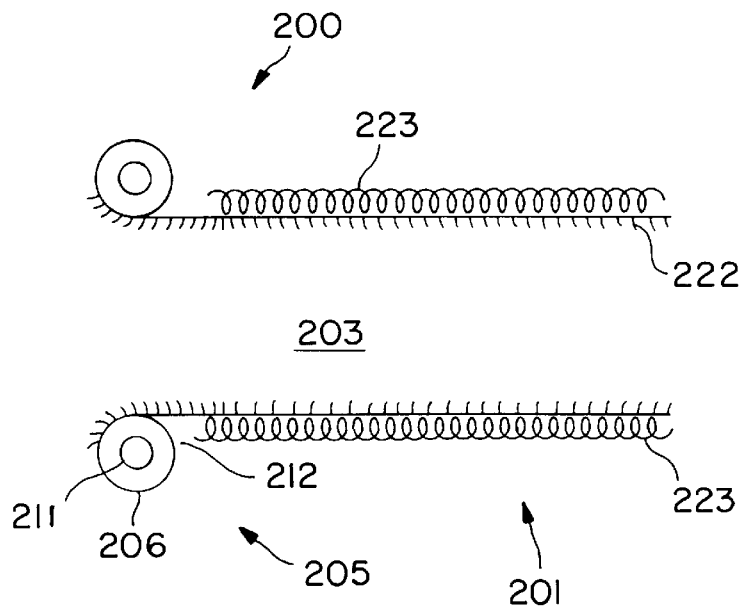
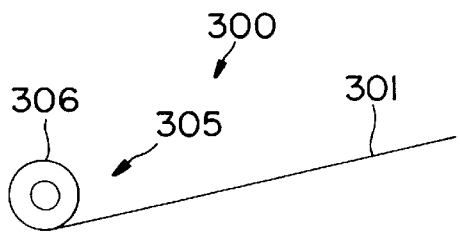
FIG. 11
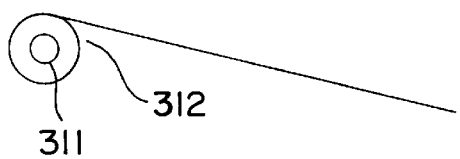
FIG. 12
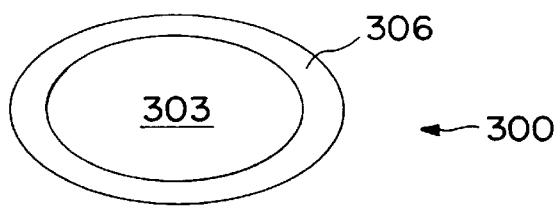
FIG. 13

CARDIAC ASSISTANCE SYSTEM

FIELD OF THE INVENTION

This invention relates to the field of cardiac assistance systems and particularly to a cardiac assistance system having an improved sewing ring to couple a skeletal muscle ventricle to the circulatory system of a patient.

BACKGROUND OF THE INVENTION

Cardiac assistance systems provide additional cardiac output in patients who suffer from insufficient cardiac output. One type of cardiac assistance system is called a left ventricular assist device (LVAD). LVADs are auxiliary pouches intended to function as booster pumps to aid the hearts of individuals suffering from chronic congestive heart failure. This condition is frequently due to heart attacks that reduce the pumping capacity of the human heart. By boosting the capacity of such a weakened heart, individuals suffering from this condition may be allowed to again lead relatively normal, effective lives.

While various designs of LVADs have been proposed, the most promising appears to be an auxiliary pouch formed from the individual's latissimus dorsi muscle and controlled by a pacemaker. This approach avoids potential rejection problems related to the use of non-autologous materials and takes advantage of well developed pacemaker and prosthetic vascular graft technology. LVADs of this type are commonly called skeletal muscle ventricles (SMVs).

To create an SMV in a human involves exposing the left latissimus dorsi muscle and dissecting the muscle free from the subcutaneous tissues and chest wall, except for the neurovascular bundle and humeral insertion. A bipolar nerve cuff electrode is placed around the thoracodorsal nerve. The nerve lead is connected to an inactive neurostimulator, buried beneath the left rectus abdominis muscle, which innervates the exposed latissimus dorsi muscle.

Next, the left chest is opened at the fourth rib. Preferably, the fourth rib is removed to provide more space for the LVAD. Optionally, the anterior pericardium is removed between the phrenic nerves and used to cover a conically-shaped mandrel of biocompatible plastic. Mandrels used for beagles had a diameter of about 3 cm, length of about 6.5 cm and volume of about 25 ml; a mandrel suitable for forming a human SMV would need to be appropriately enlarged. After wrapping the pericardium around the mandrel it is sewn to a 5 mm thick collar of synthetic material such as woven Dacron felt placed at the base of the mandrel. The dorsal edge of the latissimus dorsi muscle is then folded longitudinally upon itself and secured by sutures, after which the -medial aspect of the latissimus dorsi muscle is wrapped around the mandrel (and over the pericardium if it was used) about 2–2.5 times with the folded edge of the muscle sewn circumferentially to the Dacron sewing ring. The SMV is then positioned subcutaneously and the wound is closed and allowed to heal for three weeks.

Following this healing period, a stimulator such as the Medtronic Model 4710 is activated to transform the fatigable Type II latissimus dorsi muscle fibers to fatigue-resistant Type I muscle fibers. Typically, 6 weeks are allowed for this stimulation period, after which the chest is again opened to connect the formed muscle pouch to the aorta. This is accomplished by first attaching sensing leads to the left ventricle. The descending thoracic aorta is exposed to allow two 12 mm ringed vascular grafts to be anastomosed to the aorta, one above the other, in end-to-side fashion.

After completion of these anastomoses, the aorta between the two graft anastomoses is at least partially ligated. The plastic mandrel is removed from within the muscle pouch and a sewing ring is used to couple the pouch to the aorta. The aorta is then at least partially ligated forcing blood flow through the newly formed SMV. Finally, the nerve lead and myocardial leads are connected to an R-wave synchronous pulse-train stimulator.

One problem such past cardiac assist systems have faced, however, is with the sewing ring. Past designs of sewing rings were fabricated from a square piece of DACRON fabric into which a hole was formed. The piece of fabric was sew to the SMV and the circulatory system such that the hole permitted the inner chamber of SMV to communicate with the circulatory system. This design, however, tended not to be adequately fixed to the muscle of the SMV. In particular, because the muscle was sutured at its edge to the flat piece of fabric, the fabric or sewing ring would be subject to shear force during the contraction of the muscle. This would cause, in time, the sewing ring and SMV to detach from one another, or rupture.

SUMMARY OF THE INVENTION

This and other problems are solved by the present invention which is a system to provide cardiac assistance to a patient's heart. The system includes a pulse generator adapted to be coupled to patient's heart and adapted to be coupled to a skeletal muscle ventricle (SMV). The system further includes a sewing ring adapted to be coupled to the SMV and adapted to be coupled to the patient's circulatory system, the sewing ring has a flexible cylindrical sleeve having a distal end and a proximal end, the flexible cylindrical sleeve defining a lumen therewithin, the ring further features a means for maintaining the patency of the lumen, the means for maintaining the patency positioned on the proximal end. In the preferred embodiment the means for maintaining the patency of the lumen is a reinforcing ring mounted to the proximal end of the flexible cylindrical sleeve, preferably a silicone ring.

BRIEF DESCRIPTION OF THE DRAWINGS

FIGS. 2A–2D describe forming the SMV by wrapping latissimus dorsi muscle with or without optional pericardium around a mandrel.

FIG. 3 describes removal of the mandrel from the SMV.

FIG. 4 describes the completed SMV after attachment to the circulatory system.

FIG. 7 shows a side view of sewing ring according to the present invention.

FIG. 8 is an end view of the sewing ring shown in FIG. 7

FIG. 9 is a sectional view of the sewing ring depicted in FIG. 8.

FIG. 10 depicts a SMV using a sewing ring to provide cardiac assistance according to the present invention.

FIG. 11 is a sectional view of an alternative embodiment of a sewing ring incorporating agents on the blood contacting surface and the tissue contacting surface.

FIG. 12 is a sectional view of an alternative embodiment of a sewing ring in which the lumen is flared.

FIG. 13 is an end view of an alternative embodiment of a sewing ring in which the lumen is elliptical The Figures are not necessarily to scale.

DETAILED DESCRIPTION OF THE PREFERRED EMBODIMENTS

Figure 1:
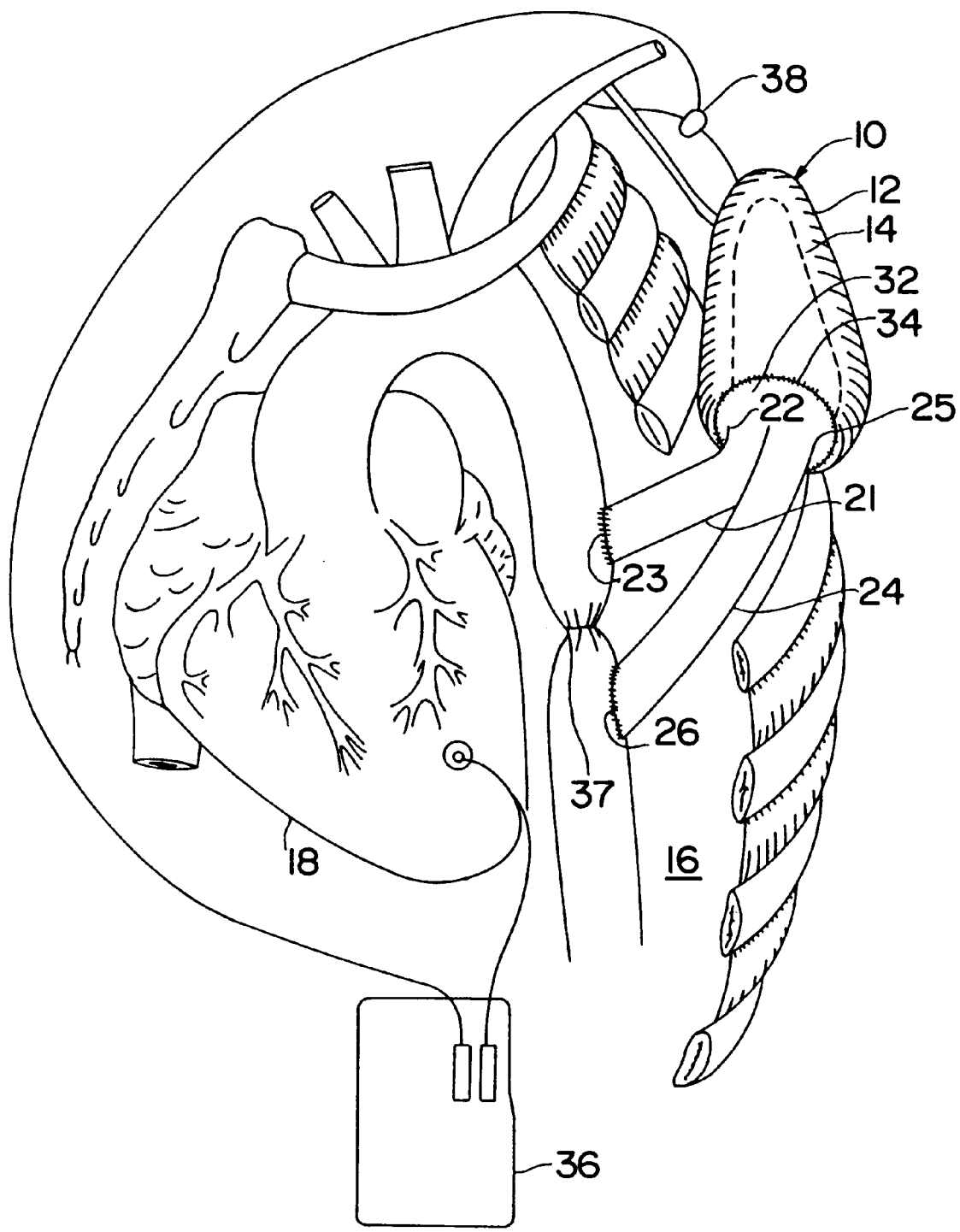
FIG. 1 describes a complete, functional LVAD.

FIG. 1 describes a typical cardiac assistance system in which a SMV 12, formed previously around a temporary mandrel to create a cavity 14, is connected to a patient's aorta 16 by ends 23 and 26 of vascular grafts 21 and 24. Opposing first ends 22 and 25 of vascular grafts 21 and 24 are sewn to a synthetic sheet of circular patch material 32 which is in turn sewn to SMV 12 at suture line 34. Ligation 37 is placed about the aorta 16 between adjacent second ends 23 and 26 of vascular grafts 21 and 24 so that the flow of blood from the heart 18 is routed through the SMV 12. Pulsing of the SMV 12 is controlled by burst pulse generator 36 connected to the heart 18 and the thoracodorsal nerve 38.

FIGS. 2A–D and FIG. 3 disclose the surgical procedure are used to create the cardiac assistance system 10. As seen in FIG. 2A a strip of latissimus dorsi muscle 62 is freed at one end but remains connected at the opposite end to the vasculature and nerve system, as is well known in the art.

Next, as seen in FIG. 2B, a plastic mandrel 41 and sewing ring 100 are assembled together. Sewing ring is passively held in place within mandrel at this stage. Inflatable mandrel 41 is made of a biocompatible material, such as silicone or polyurethane. Mandrel is filled with a fluid, typically saline, using a needle and syringe inserted into a filler port 42 which, in turn, is connected to mandrel by tube 43.

Next as seen in FIG. 2C the muscle 62 is wrapped around the mandrel 41; typically 2–2.5 wraps of latissimus dorsi muscle are used. An alternative approach may also be used whereby a sheet of anterior pericardium, previously removed from between the phrenic nerves, is wrapped around mandrel prior to wrapping the latissimus dorsi muscle 62 around mandrel 41 to create the SMV 12.

As seen in FIG. 2D the muscle is nerve 38 is coupled to a pulse generator by lead 99 and the muscle is then trained for a period of 6–8 weeks, as is well known in the art.

Finally, as seen in FIG. 3 the mandrel is deflated and removed from the SMV 12 and vascular grafts 21 and 24 are coupled to aorta 16 and the sewing ring 100 by one or more sutures 98, all of which is known in the art. After completion of these steps the LVAD is activated before closing the patient's chest.

FIG. 4 shows a completed SMV coupled to the aorta by vascular grafts 21 and 24 and to pulse generator.

Figure 5:
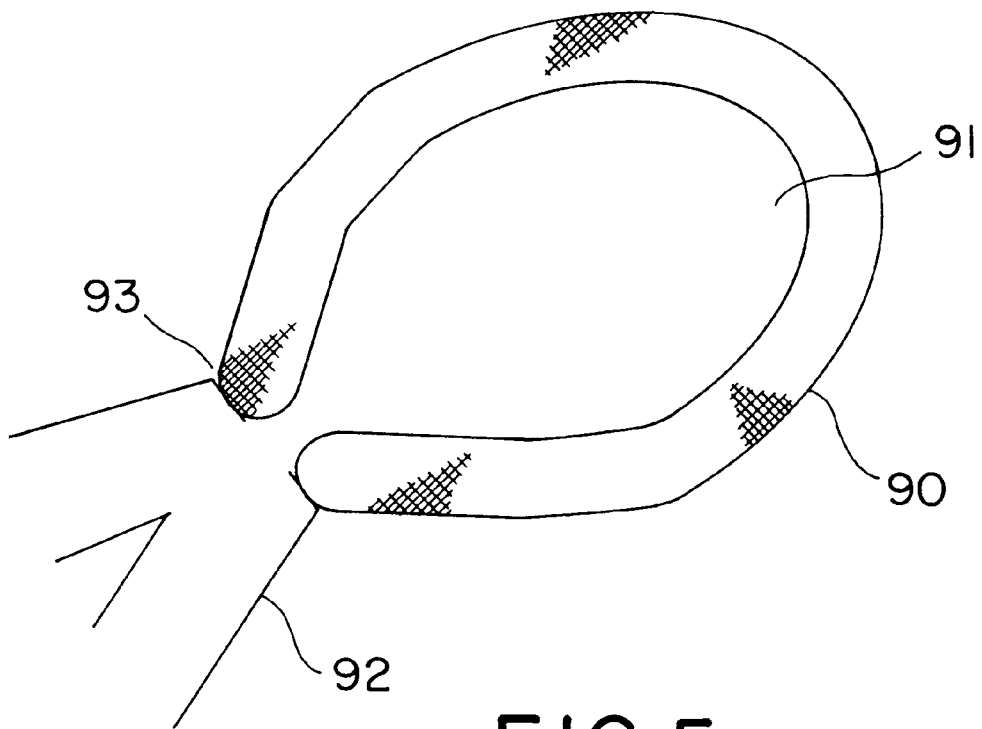
FIG. 5 is a sectional view of a SMV featuring a past design for a sewing ring.

FIG. 5 is a sectional view of a SMV featuring a past design for a sewing ring. As seen, the SMV of a cardiac assistance system is created by forming a muscle 90 to have a chamber 91 which is coupled to the circulatory system 92 using a sewing ring 93.

Figure 6:
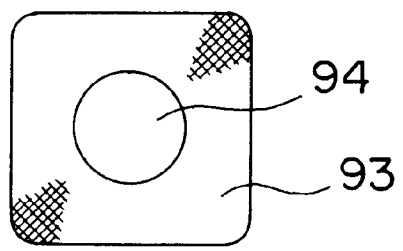
FIG. 6 is a plan view of a sewing ring of the prior art.

FIG. 6 is a plan view of a sewing ring of the prior art. As seen past designs of sewing rings were fabricated from a square piece of DACRON fabric 93 into which a hole 94 was formed. Hole was used to couple chamber of SMV to the circulatory system. This design, however, tended not to be adequately fixed to the muscle. As can be appreciated, the sewing ring would be subject to shear force during the contraction of the SMV. This would cause, in time, the ring and SMV to detach from one another, or rupture.

FIG. 7 shows a side view of sewing ring 100 according to the present invention. As seen, sewing ring has essentially two portions, a cylindrical portion 101 and a ridge portion 106. A lumen 103 is defined within each respective portion as best seen in FIG. 8. Lumen is circular in the preferred embodiment although other shapes may also be used, e.g. elliptical.

FIG. 9 is a sectional view of the sewing ring depicted in FIG. 8. In the preferred embodiment, cylindrical portion is integral with ridge 106. Ridge is formed by folding the material used for cylinder around a reinforcing ring 111 and suturing the material to itself at point 112. Reinforcing ring is provided for maintaining the patency of the lumen. In the preferred embodiment a silicone ring is used for the reinforcing ring and DACRON is used as the fabric for cylindrical portion. In the preferred embodiment lumen has a diameter "D" which is greater than or equal to the length "L" of sewing ring.

FIG. 10 depicts a SMV using a sewing ring to provide cardiac assistance according to the present invention. As seen, SMV 90 may be sutured along a large surface area of cylindrical portion 101 to ridge 106. Thus the sewing ring is not subject to shear force during the contraction of the muscle, but instead is subject to compressor force by the muscles which tend to only increase the adhesion between the muscle and the sewing ring.

Sewing ring of the present invention may further feature the incorporation of pharmacological agents for controlled release into the surrounding tissues to promote permit healing and adhesion of the muscle to the ring. Such agents would include growth factors or anti inflammatory or anabolic agents, such as various steroids, for example. Moreover, additional agents to inhibit thrombogenesis or calcification may likewise be incorporated into the fabric, such as a fibrin glue coating or papaverine or gluteraldehyde. Various bioactive molecules, such as heparin, may likewise be used for example. Such agents may be located within either the fabric portion of the sewing ring or the reinforcing ring. These agents may be incorporated singly or in any suitable mixture thereof.

Many methods of incorporating such agents into the sewing ring may be used, including solvent swelling, co-solvent casting, compression molding, microencapsulation, polymerization or covalent bonding. The agents may be either directly combined with the material, coated thereon or coupled. It is most preferred if the incorporated agent or agents are incorporated such that they may be released during the 6–8 week period of training of the SMV.

FIG. 11 shows a sectional view of an alternative embodiment of a sewing ring 200 incorporating such agents. As seen, sewing ring is the same as that described above. That is sewing ring has essentially two portions, a cylindrical portion 201 and a ridge portion 205. A lumen 203 is defined within each respective portion. The lumen is circular in the preferred embodiment although other shapes may also be used, e.g. elliptical, Cylindrical portion 201 is integral with ridge 205. Ridge 205 is formed by folding the material used for cylinder around a reinforcing ring 211 and suturing the material to itself at point 212. In the preferred embodiment a silicone ring is used for the reinforcing ring and DACRON is used as the fabric for cylindrical portion. In this embodiment blood contacting inner surface has heparin attached thereon 222 and muscle contacting outer surface has the anti inflammatory steroid beclamethasone thereon. Of course, as discussed above various other agents, alone or in combination, may also be used. These agents may further be placed within or upon silicone ring.

FIG. 12 shows a sectional view of an alternative embodiment of a sewing ring 300. As seen, sewing ring differs from that described above through a flared sides.

FIG. 13 is an end view of an alternative embodiment of a sewing ring 300 in which the lumen 303 is elliptical.

Although the invention has been described in detail with particular reference to a preferred embodiment and alternate embodiments thereof, it will be understood variations and modifications can be effected within the scope of the following claims. For example, although illustrated within the context of pouch shaped SMVs, the present invention may also be used in other type of LVADs, such as tube SMVs. Such modifications may include substituting elements or components which perform substantially the same function in substantially the same way to achieve substantially the same result for those described herein.

What is claimed is:

1. A system for providing cardiac assistance to a patient's heart, comprising
    a pulse generator adapted to be coupled to patient's heart and a skeletal muscle ventricle; and
    a sewing ring adapted to be coupled to the skeletal muscle ventricle and a patient's circulatory system, the sewing ring comprising a flexible cylindrical sleeve having a distal end and a proximal end, the flexible cylindrical sleeve comprising means for maintaining the patency of the lumen defining a lumen therewithin, the means for maintaining the patency being positioned on the proximal end.

2. A system for providing cardiac assistance to a patient's heart according to claim 1, wherein the means for maintaining the patency of the lumen comprises a reinforcing ring mounted to the proximal end of the flexible cylindrical sleeve.

3. A system for providing cardiac assistance to a patient's heart according to claim 1, wherein the means for maintaining the patency of the lumen comprises a fold in the flexible cylindrical sleeve having an edge, the edge of the fold being attached to the flexible cylindrical sleeve, the fold defining an annular cavity therein, a reinforcing ring positioned within the annular cavity.

4. A system for providing cardiac assistance to a patient's heart according to claim 1, wherein the lumen has a diameter and the sewing ring has a length, the length being equal to ot greater than the diameter.

5. A system for providing cardiac assistance to a patient's heart according to claim 1, wherein the reinforcing member is a silicone ring.

6. A system for providing cardiac assistance to a patient's heart according to claim 5, wherein the silicone ring and the flexible cylindrical sleeve have one or more pharmaceutical agents loaded therein.

7. A system for providing cardiac assistance to a patient's heart according to claim 1, wherein the lumen is flared and has a first diameter and a second diameter, the first diameter being greater than the second diameter.

8. A system for providing cardiac assistance to a patient's heart according to claim 1, wherein the lumen is elliptical.

9. A system for providing cardiac assistance to a patient's heart, comprising
    a pulse generator adapted to be coupled to patient's heart and to a skeletal muscle ventricle; and
    a sewing ring adapted to be coupled to the skeletal muscle ventricle and a patient's circulatory system, the sewing ring comprising a flexible sleeve comprising a biocompatible material, the flexible sleeve having at a first end thereof a fold having an edge, the edge being attached to the flexible sleeve, thc fold defining an annular cavity therein, a reinforcing ring being positioned within the annular cavity.

10. A system for providing cardiac assistance to a patient's heart according to claim 9, wherein the lumen has a diameter and the sewing ring has a length, the length being equal to or greater than the diameter.

11. A system for providing cardiac assistance to a patient's heart according to claim 9, wherein the reinforcing member is a silicone ring.

12. A system for providing cardiac assistance to a patient's heart according to claim 11, wherein the silicone ring and the flexible sleeve have one or more pharmaceutical agents loaded therein.

13. A system for providing cardiac assistance to a patient's heart according to claim 9, wherein the lumen is flared and has a first diameter and a second diameter, the first diameter being greater than the second diameter.

14. A system for providing cardiac assistance to a patient's heart according to claim 9, wherein the lumen is elliptical.

15. A system for providing cardiac assistance to a patient's heart, comprising
    a pulse generator adapted to bc coupled to patient's heart and to a skeletal muscle ventricle; and
    a sewing ring adapted to be coupled to the skeletal muscle ventricle and a patient's circulatory system, the sewing ring comprising a flexible sleeve comprising a biocompatible material, the flexible sleeve defining a lumen, the flexible sleeve having one or more pharmaceutical agents loaded therein.

16. A system for providing cardiac assistance to a patient's heart according to claim 15, wherein the flexible sleeve comprises a first blood-contacting surface having an anti-thrombogenic agent disposed thereon and a second tissue-contacting surface having an anti-inflammatory agent disposed thereon.

17. A system for providing cardiac assistance to a patient's heart according to claim 15, wherein the flexible sleeve comprises at a first end thereof a fold having an edge, the edge being attached to the flexible sleeve, the fold defining an annular cavity therein, a reinforcing ring being positioned within the annular cavity.

18. A system for providing cardiac assistance to a patient's heart according to claim 17, wherein the reinforcing member is a silicone ring.

19. A system for providing cardiac assistance to a patient's heart according to claim 15, wherein the lumen has a diameter and the sewing ring has a length, the length being equal to or greater than the diameter.

20. A system for providing cardiac assistance to a patient's heart according to claim 15, wherein the lumen is flared and has a first diameter and a second diameter, the first diameter greater than the second diameter.

21. A system for providing cardiac assistance to a patient's heart according to claim 15, wherein the lumen is elliptical.

* * * * *